United States Patent [19]

Korth

[11] Patent Number: 4,974,219
[45] Date of Patent: Nov. 27, 1990

[54] POLARIZING BEAM SPLITTER USING DIELECTRIC MULTILAYERS

[75] Inventor: Hans-Erdmann Korth, Stuttgart, Fed. Rep. of Germany

[73] Assignee: International Business Machines, Armonk, N.Y.

[21] Appl. No.: 168,792

[22] Filed: Mar. 16, 1988

[30] Foreign Application Priority Data

Oct. 30, 1987 [EP] European Pat. Off. .......... 87115966

[51] Int. Cl.$^5$ .......................... G11B 7/12; G11B 7/135
[52] U.S. Cl. ..................................... 369/13; 369/110; 360/114; 350/370; 350/381
[58] Field of Search ................... 369/13, 110; 350/370, 350/381, 394; 360/59, 114; 365/122

[56] References Cited

U.S. PATENT DOCUMENTS

| | | | |
|---|---|---|---|
| 3,597,047 | 8/1971 | Carbrey | 350/381 |
| 4,239,337 | 12/1980 | Campbell et al. | 350/381 |
| 4,252,410 | 2/1981 | Jain | 350/394 |
| 4,507,766 | 3/1985 | Saimi et al. | 369/110 |
| 4,841,510 | 6/1989 | Yoshizawa | 369/110 |

FOREIGN PATENT DOCUMENTS

| | | |
|---|---|---|
| 0100178 | 2/1984 | European Pat. Off. . |
| 0226647 | 7/1987 | European Pat. Off. . |
| 52-60111 | 5/1977 | Japan .................................. 360/114 |
| 60-118803 | 6/1985 | Japan . |
| 61-243962 | 10/1986 | Japan . |
| 62-14340 | 1/1987 | Japan . |

OTHER PUBLICATIONS

IBM Technical Disclosure Bulletin, "Method for Reading Magneto-Optical Storage Media", vol. 29, No. 4, Sep. 1986, pp. 1871–1872.

Primary Examiner—Stuart S. Levy
Assistant Examiner—Hoa Nguyen
Attorney, Agent, or Firm—James A. Pershon

[57] ABSTRACT

An optical analyzer for determining changes of the polarization plane in a light beam (4) comprises a substrate (20) supporting a photodetector array (21) and a system of imaging mirrors (22–24) underneath a parallel plate (25) of high-quality optical glass. The lower surface of the glass plate is covered by a system (26) of dielectric multilayers which acts as a polarizing beam splitter over a large range of angles of incidence. The optical beam (4) enters the analyzer through the glass plate to impinge under an oblique angle of incidence on a first mirror (24) which rotates the plane of polarization in the beam by 45 degrees with respect to the polarizing beam splitter, which then generates two beams partial (202,203) to be eventually directed to photodetector array (21). The beam analyzer is used in magneto-optical storage system to extract an information signal and to generate servo control signals for the focus and track positions of the beam. The tilted first mirror may have circular or stripe geometry and be integrally formed within the substrate (20). The multilayer polarizing beam-splitter system comprises two stacks of layers separated by an intermediate layer and covered by a thick dielectric layer.

5 Claims, 9 Drawing Sheets

POLARIZING BEAM SPLITTER USING DIELECTRIC MULTILAYERS

TECHNICAL FIELD OF THE INVENTION

The invention relates to analyzers for determining the polarization state in beams of light; a preferred field of use is in optical storage devices, in particular in magnetooptic disks.

BACKGROUND OF THE INVENTION

Optical storage devices use information carriers with high density of recording, which are written and read out by focussed laser beams. A promising technique for rewritable optical data recording is magnetooptic storage, in particular, magnetooptic disks with random-access capability. In magnetooptic storage media, data bits are written into concentric or spiral tracks by laser heating tiny spots of a thin, axially-magnetized layer on a disk substrate above the so-called Curie temperature. Upon cooling in the presence of an external magnetic field, which is oriented opposite to the axial magnetization, the heated spots will reverse their magnetization direction and form information indicia with dimensions in the micrometer range.

The recorded information is retrieved by reflecting a focussed, low-power laser beam on the track and sensing the rotation of the plane of polarization in the reflected light, which occurs when the laser beam passes through a spot of reversed magnetization. The angles of rotation in this "magnetooptic-Kerr effect" are very small and in the order of degrees of arc. A similar technique for reading out magnetooptic media uses the Faraday effect in light that is transmitted through a transparent magnetooptic layer.

In addition to extracting data information, the analysis of the reflected light beam must yield servo control signals for maintaining the readout beam focussed and locked in the tracks of data bits. In conventional devices for magnetooptic storage, this analysis was performed by an optical system with a considerable number of high-quality components that are bulky, expensive and difficult to adjust. Examples of such optical beam analyzing systems can be found, e.g., in EP-A-No. 156460 or DE-A-No. 3334120.

EP-A-No. 226647 discloses a read/write head for an optical disk, which avoids individual optical components and integrates the beam-analyzing function (with beam splitter, beam-shaping elements and photodetectors) into the light-guiding access arm for the optical disk. This integrated access arm is, however, difficult to manufacture and does not yet achieve an optimum mass distribution of the access arm which is required for high-access speed to selected data tracks.

SUMMARY OF THE INVENTION

It is, therefore, the object of the invention to provide an analyzer for determining the polarization state in beams of light, which is embodied in one small, lightweight and easy-to-manufacture component and can be used in particular for optical storage devices.

A further object of the invention is to provide a polarizing, beam-splitter layer, which is effective for entry beams with a wide range of angles of incidence and can be used in the beam analyzer of the invention.

These objects are achieved by the invention as defined in the claims embodiments of the invention are characterized in the dependent claims.

The proposed polarization-sensitive beam analyzer integrates the optical and electrical components into a simple package, e.g. a standard IC package, and requires only one component of high optical quality, viz. a parallel glass plate with a multilayer system that acts as a polarizing beam splitter and is insensitive to variations in angles of incidence. The orientation of the glass plate in the optical system of the access arm for an optical disk is chosen such that it reflects most of the incoming polarized laser beam to the information-carrying surface, and then geometrically separates the information-carrying light components in the reflected beam whose plane of polarization is perpendicular to the incoming laser light. The information-carrying beam is directed to a tilted system of reflectors (either circular or in stripes), which further rotates the plane of polarization in the information-carrying beam by 45 degrees. Upon reflection at the polarizing beam-splitter (PBS) layer, the information-carrying beam is split into partial beams that are directed to separate photodetectors for extracting the data signal. Additional portions of the information-carrying beam are directed to further photodetectors for generating focus and track servo control signals; peripheral portions of the beam are sufficient for this purpose.

The beam-shaping elements of the beam analyzer, like plane and curved mirrors underneath the parallel glass plate, may be directly formed in the package, which also receives the photodetectors whose leads will be connected to the pins of the IC package.

The three functional elements of the beam analyzer (the parallel glass plate with polarizing beam splitter PBS, the IC package with the beam forming elements and the photodetector array) can be manufactured in parallel processes at very low cost. Assembly is simple and requires only very little alignment.

The polarizing beam-splitter PBS system on the parallel glass plate consists preferably of a novel system of alternate dielectric layers, which are arranged in two stacks separated by an intermediate layer of the lower-index material and higher thickness. A top layer sequence may include a thick layer of the low-index material and two alternating layers of small thickness. Such a layer system exhibits a high separation for the two polarization directions over a large range of incident angles.

DESCRIPTION OF THE FIGURES

In the diagrams, like reference numerals refer to the same elements.

DESCRIPTION OF THE PREFERRED EMBODIMENT

Figure 1:
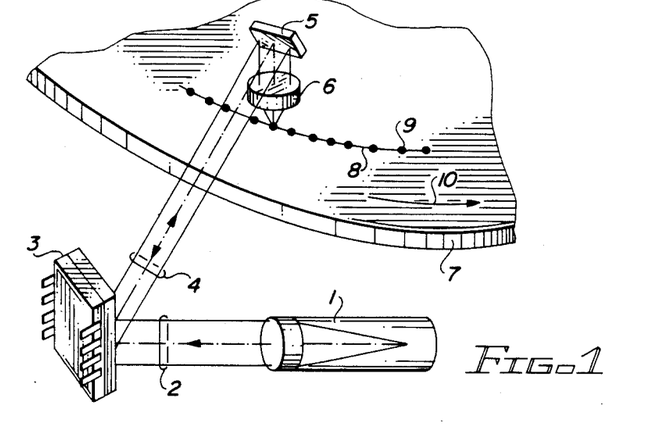
FIG. 1 shows a schematic perspective view of an optical access system for a magnetooptic disk storage using a beam analyzer in accordance with the invention.

FIG. 1 shows in schematic view the overall arrangement of an optical system to read out data from a magnetooptical disk 7; the data is stored as indicia or tiny spots 9 arranged in circular tracks 8 moving in direction of arrow 10. Track 8 may be shallow grooves with center-to-center spacings in the micrometer range formed in the substrate supporting the magnetooptic layer.

The optical setup consists of a laser 1 with suitable optics to generate a collimated beam 2, which impinges on integrated beam analyzer IBA 3 and is reflected, as beam 4, to deflection mirror 5 and focussing lens 6. The focussed beam is retroreflected at the magnetooptic layer on disk 7 and returns along the path of beam 4 to integrated beam analyzer IBA 3, which generates electrical output signals representing the stored data, as well as the focus condition of lens 6 and the position of the focussed beam with respect to track 8. The two latter signals are used for servo control of track and focus of beam 4.

The optical system of FIG. 1, or its equivalents, may be mounted on the rotary access arm disclosed in European Pat. Application No. 86 118 169.1.

Figure 2A:
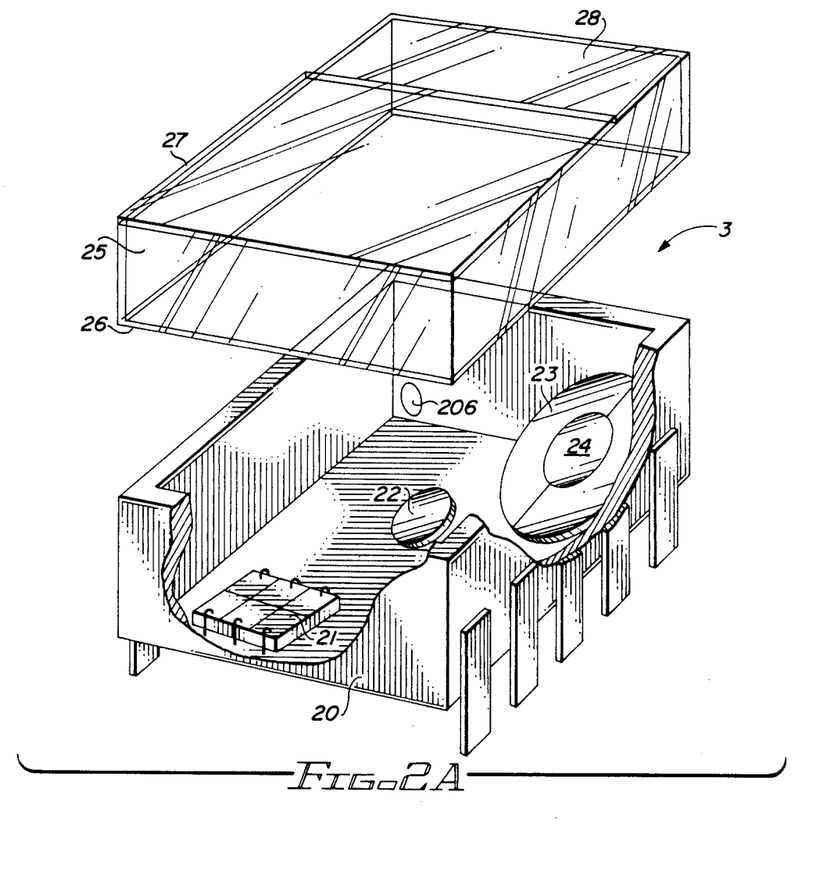
FIG. 2A shows a schematic perspective-exploded view of the beam analyzer in FIG. 1.

FIG. 2A shows an exploded schematic view of the integrated beam analyzer IBA 3, which consists of a substrate 20 with electrical contact pins, electrically connected to contact pads of a photodetector array 21 which is arranged at the inside bottom of substrate 20. The dimensions and the positions of the contact pins are conveniently chosen to be compatible with known integrated circuits (IC) packages, e.g. a conventional dual in-line IC package (DIP).

In the interior of box-like substrate 20, optical-reflective elements 22, 23, 24 are arranged either as separate elements, or formed integrally within substrate 20; in the latter case, they will preferably be covered with metallic layers for increased reflectivity and reduced influence on the polarization states of the light beams.

The top side of substrate 20 is covered and closed by a parallel plate 25 of high-quality, optical glass on whose lower surface (pointing to the optical elements 22, 23, 24) a system of dielectric layers 26 is deposited which acts as a polarizing beam splitter PBS. The system of layers 26 is shown in more detail in FIGS. 12A and 12B using the materials and thickness shown in Tables I and II, respectively.

The top side of glass plate 25 (i.e. the side pointing away from substrate 20), is covered with a reflection layer 27 in a window area that is not affected by the incoming and reflected beams 2 and 4. The window area 28 for beams 2,4 can be covered by an anti-reflective layer.

Figure 2B:
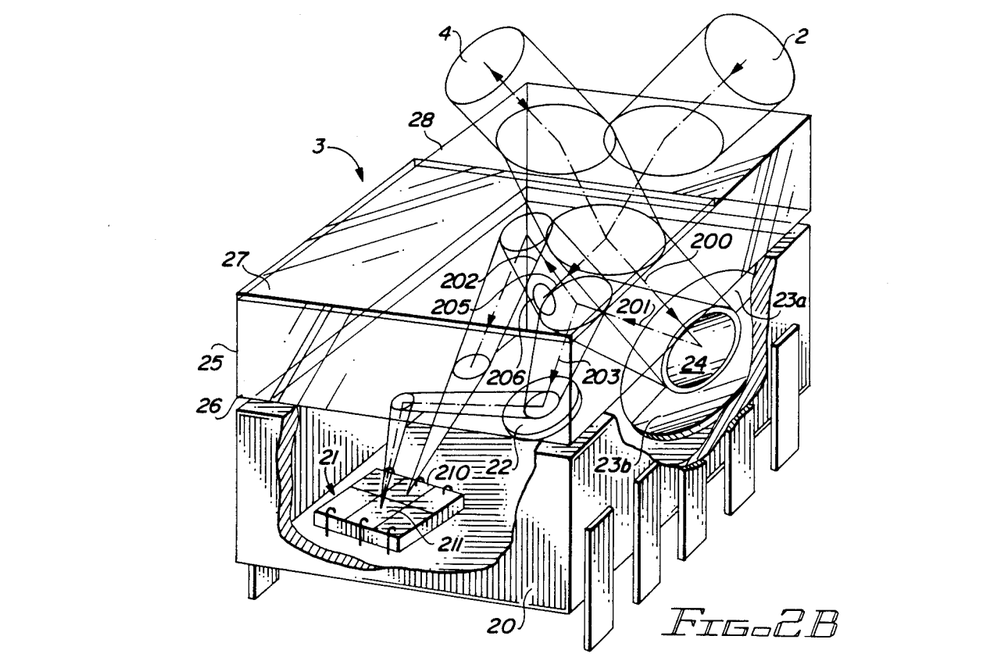
FIG. 2B shows the beam analyzer of FIG. 2A, supplemented by schematic paths of the light beams for reading out information stored in a magnetooptic storage medium.

FIG. 2B shows the beam analyzer of FIG. 2A in assembled form and indicates in a schematic way the paths of the two partial beams that are required to extract the data signal from the information-carrying laser beam. The incoming laser beam 2 impinges on the top surface of parallel glass plate 25 at a peripheral portion and outside the area covered by reflective coating 27. The polarization direction of laser beam 2 is chosen such that this beam is reflected almost entirely at polarizing beam-splitter layer 26 and exits plate 25 as beam 4; incoming light transmitted through PBS 26 is wasted and can be monitored by a photodetector 206. After reflection at the magnetooptic disk, the recollimated beam 4 returns along the same path, but with a slight rotation in its plane of polarization due to the Kerr effect occurring upon reflection at a magnetooptic surface with vertical magnetization. Polarizing beam-splitting PBS layer 26 reflects most of the light with the original direction of polarization in beam 4 back along the path of beam 2, whereas beam components with a plane of polarization orthogonal thereto are passed through PBS layer 26 onto a system of tilted mirrors 23a, 23b, 24.

For the beam returning from the optical disk, PBS layer 26 acts thus as a "leaky" beam splitter to obtain a beam with an optimal mix of polarization directions for evaluating the Kerr signal, either in conventional ways or by the method described in EP-A-No. 0226647. Some 60–80% of the light returning from the optical disk with unchanged polarization direction should be transmitted by PBS layer 26 for signal evaluation and all of the light whose direction of polarization has been rotated by the Kerr effect. This ratio is achieved by the PBS layers, to be described later, when an angle of incidence of some 50 degrees is chosen for returning beam 4. For further discussion of the beam paths within beam analyzer 3, reference is made to the central rays of the beams, e.g. ray 200 for the beam incident on mirror system 23a, 23b and 24.

Tilted mirror system 23a, 23b and 24 acts to deflect the light beam 200 out of the plane of incidence so that the polarization of the reflected beam 201 will be rotated by 45 degrees with respect to the PBS layer 26. Therefore, when beam 201 hits PBS layer 26 again, two beams 202, 203 are generated, beam 202 entering glass plate 25, and beam 203 being reflected to mirror 22 arranged at the interior bottom of substrate 20.

PBS layer 26 must be configured such that splitting of beam 201 is effected without losses; if the angle of incidence for beam 201 is chosen in the order of 60-70 degrees, the PBS layer in Tables I and II and FIGS. 12a and 12b structure to be described later meets this requirement. Thus the same PBS layer allows "leaky" and "nonleaky" beam splitting, controlled by the angle of incidence.

Beam 203 eventually reaches photodetector 210 (after a further reflection at PBS layer 26), whereas beam 202 is totally reflected at the reflective top layer 27 of glass plate 25 and eventually reaches photodetector 211 in photodetector assembly 21. Both beams 202, 203 are focussed on photodetectors 210 and 211, respectively, because mirror 24 has imaging properties, e.g. a spherical or parabolic surface. Mirror 22 may also have imaging properties, or may be a plane mirror as the rather great surfaces of photodetectors in array 21 do not require precise beam control.

In an ideal configuration, mirrors 24 and 22 are formed as conjugate surfaces, wherein mirror 24 is shaped to compensate for the astigmatism which is introduced when convergent beam 202 passes obliquely through glass plate 25, and mirror 22 compensates for the distortion introduced by mirror 24 in beam 203, which does not pass glass plate 25. Further, mirror 22 secures roughly equal optical path lengths for beams 202 and 203.

The beam parts reflected at the annular mirrors 23a,b, which eventually reach the other photodetectors in array 21, are not shown in the diagram of FIG. 2B and will be discussed later. Mirrors 23a and b may also have imaging properties to focus the peripheral beam portions onto associated photodetectors.

Figure 3A:
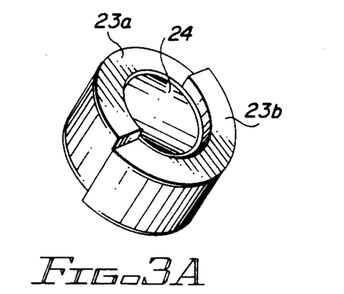
FIGS. 3A,B show schematic and perspective diagrams of mirror elements to be mounted into the beam analyzer of the invention.
Figure 3B:
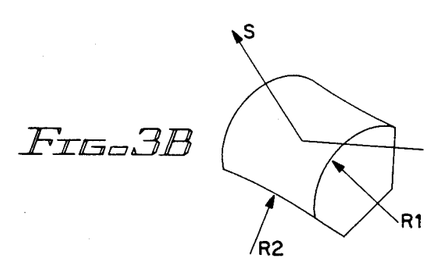

In one embodiment, mirrors 22-24 were manufactured as individual components and inserted into substrate 20. Mirror 24 was a spherical concave mirror (r=20 mm), as well as mirrors 23a,b. Two slightly tilted concave half-rings 23a,b were used in this embodiment (FIG. 3A). Mirror 22 was a convex toroidal mirror with radii $r_1 = 8$ mm, $r_2 = 30$ mm (FIG. 3B). The path of the reflected beam is indicated by vector S.

The diameter of beams 2,4 was of the order of 5 mm; the range of angles of incidence on PBS layer 26 was then approximately ±9 degrees.

Figure 2C:
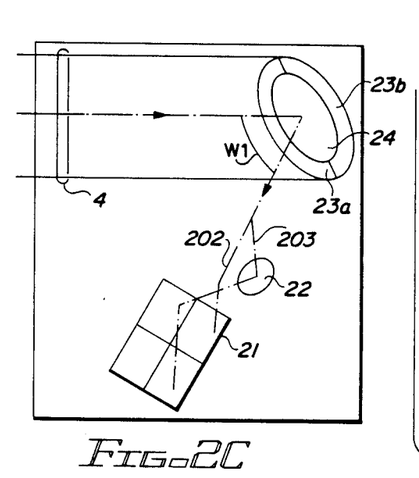
FIG. 2C shows a schematic top view of the beam analyzer in FIG. 2B.
Figure 2D:
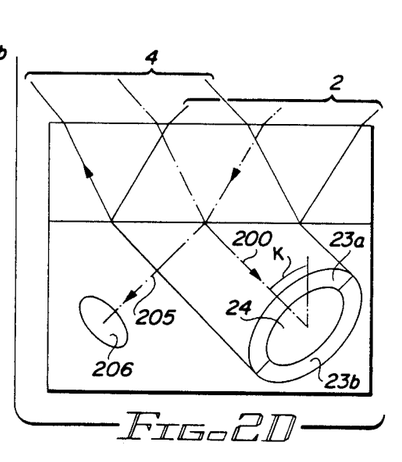
FIG. 2D shows a schematic side view of the beam analyzer in FIG. 2B in the plane of the incident beams.
Figure 2E:
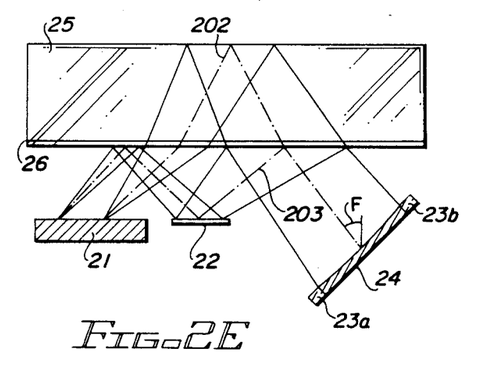
FIG. 2E shows a schematic section through the beam analyzer in FIG. 2B along the plane of the beams propagating in the interior of the analyzer.

FIGS. 2C-2E show simplified views of beam analyzer 3 from the top (FIG. 2C), in the plane of the incident laser beams 2,4 (FIG. 2D) and in the plane of the beam reflected at tilted mirror 24 (FIG. 2E) to further illustrate the beam paths in the interior of beam analyzer 3.

Figure 10:
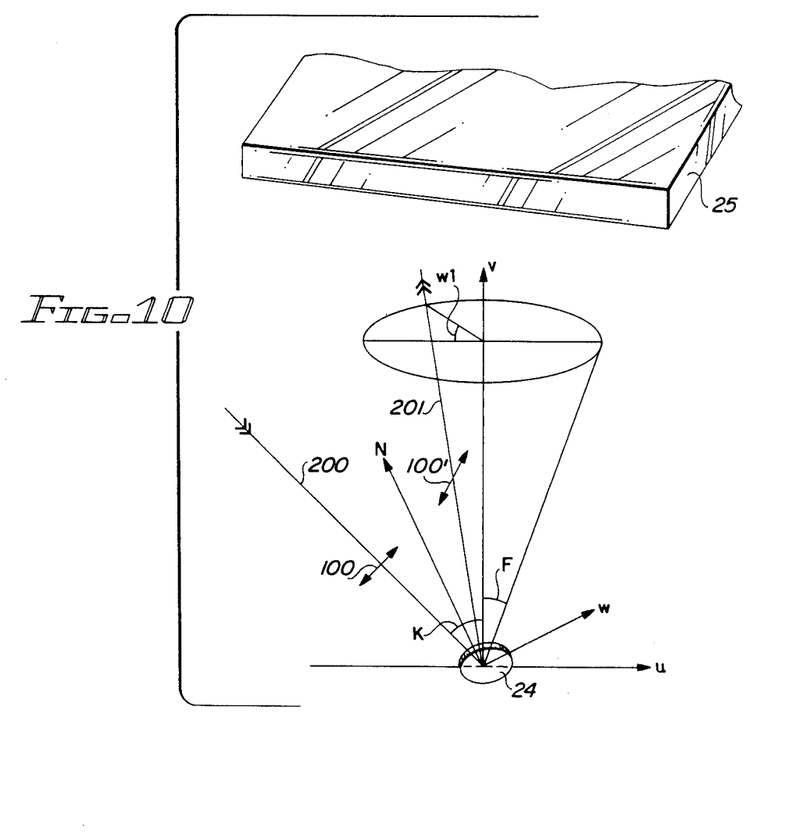
FIG. 10 shows a geometrical diagram to illustrate the rotation of the polarization plane upon reflection at a tilted mirror.

The orientation of reflected beam 201 (and thus of the tilted mirror 24) is indicated in FIGS. 2C-E by angles W1, K and F. Angle W1 designates the rotation of beam 201 after reflection at tilted mirror 24, angle K the inclination of the incident beam 200, and F the angle included between the reflected beam 201 and the normal to the PBS layer system 26. These angles are also indicated in FIG. 10, which represents a schematic perspective diagram for the reflection of incident beam 200 at mirror 24 located at the origin of a reference system, whose v-axis is the normal to glass plate 25. The normal N to mirror 24 points outside to the back of the plane of the drawing. The polarization vector 100 of incident beam is rotated to vector 100' upon reflection of the beam.

To obtain the desired rotation of ±45° in the plane of polarization, two orientations of the beams are available (for an angle of incidence K=45°):

| W1 = 60,725° | with F = 40,79° |
| W1 = 147,35° | with F = 15,70° |

Figure 7A:
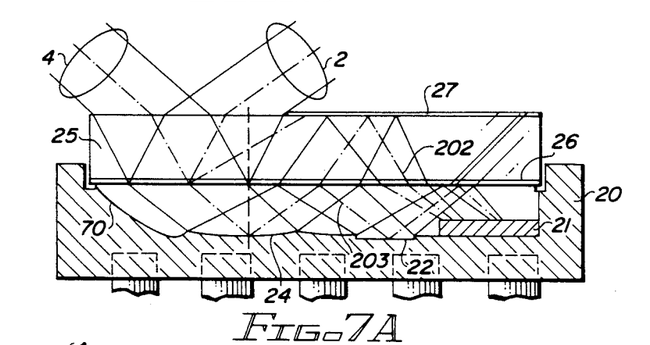
FIGS. 7A,B show schematically an alternate arrangement for the components of the beam analyzer according to the invention in a sectional and a top view, respectively.
Figure 7B:
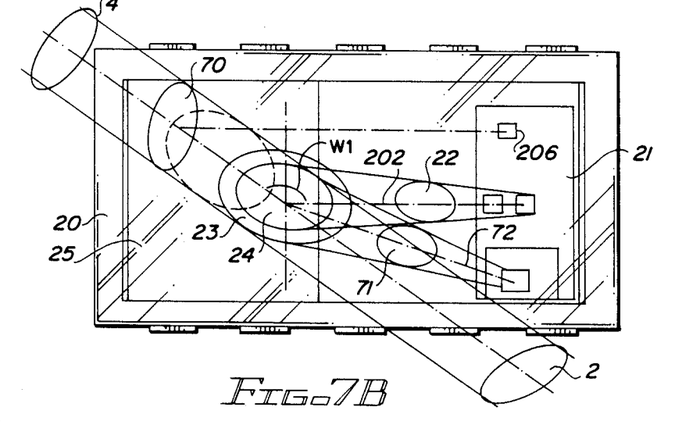

The embodiment of FIGS. 2A-E represents the first alternative and FIGS. 7A and B the alternate embodiment of the beam analyzer when the incident and the information-carrying beams are oriented under W1=147,35°. Reference numerals 70,71 designate additional mirrors for wasted light and the servo beam parts respectively; reference numeral 72 identifies the central ray of the servo beams.

Figure 4:
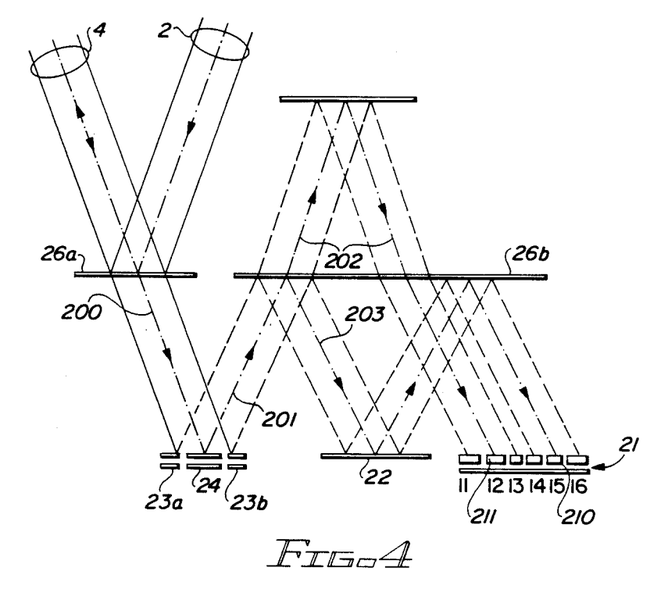
FIG. 4 shows schematically the unfolded beam path of FIG. 2B.

FIG. 4 shows the beam paths of beam analyzer 3 folded into a common plane. Interface 26a represents that part of PBS layer 26 onto which the incoming laser beam 2 impinges and interface 26b the part of PBS layer 26, which is reached by the partial beams after they have been reflected at tilted mirrors 23, 24, which acted to rotate their plane of polarization by 45 degrees. In addition to the beams shown in FIG. 2B, the peripheral beams reflected at annular mirrors 23a, 23b are also indicated schematically together with the photodetectors onto which they impinge.

Figures 5A, 5B:
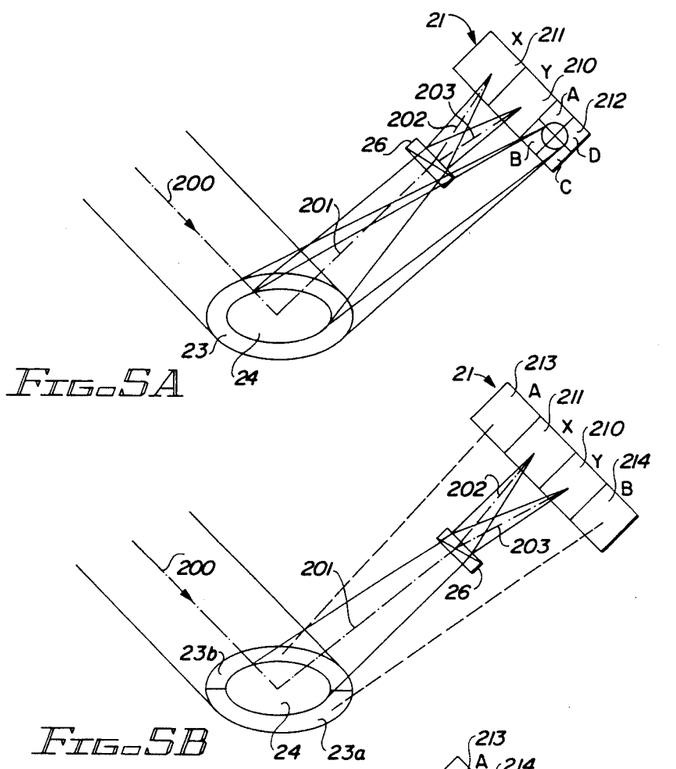
FIGS. 5A–C show in schematic and unfolded representation the paths of the beams in various embodiments that are used for data readout and beam-position servo control.
Figure 5C:
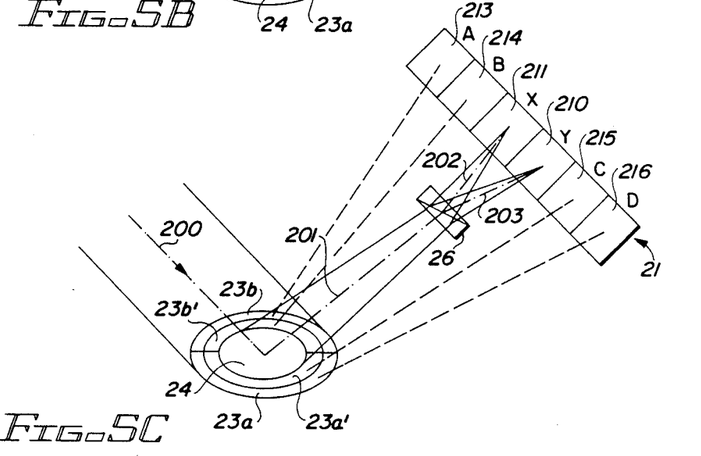

FIGS. 5A-C show different arrangements for the annular mirror elements 23a and b in tilted mirror system 23, 24 and the concomitant layout of photodetectors in array 21; the toroidal beams generated by the annular mirrors 23a and b are indicated very schematically and without the beam doubling occurring at PBS 26 (to reduce the complexity of the diagrams). The polarizing beam-splitter layer 26 is schematically indicated by the symbol of an equivalent birefringent plate.

In FIG. 5A, the peripheral parts of impinging beam 200 are reflected by an astigmatic (elliptically shaped), annular focussing surface 23 to a four-quadrant photodiode array 212 29 with four photodetectors A-D to generate focus and track information in the conventional way from changes in the beam shape due to defocussing and track misalignment.

In FIG. 5B, the annular mirror is subdivided into two concentric reflectors 23a,23b, which are titled with respect to each other and focus the annular portions of beam 200 to photodetectors 213 and 214, respectively. This divided arrangement provides better sensitivity and a less critical alignment than the arrangement of FIG. 5A. Still enhanced sensitivity is achieved when both annular mirrors 23a,23b are doubled along their peripheral direction, each half sending light to an associated photodetector 214,215 and 213,216, respectively (FIG. 5C). The detectors are arranged in the far field of the imaging system and generate a signal whenever the beams expand or contract.

The physical beam splitting for data and servo signals, achieved by the arrangements of FIGS. 5A-C exploits the fact that most of the servo information is contained in the outer zone of the light beam. The data signal is extracted in all embodiments of FIGS. 5A-C from the outputs x and y of the data photodetectors 211 and 210, respectively, according to the following relation:

$$Data\ signal = x - y$$

In the arrangement of FIG. 5A and FIG. 5C, the control signals are obtained from the outputs of the servo photodetectors in the following way:

$$\text{Focus signal} = (A+D) - (B+C)$$

$$\text{Track signal} = (A+B) - (C+D)$$

In the arrangement of FIG. 5B, the control signals are:

$$\text{Focus signal} = (A+B) - (X+Y)$$

$$\text{Track signal} = (A-B)$$

The focus error signal and the track error signal are thus obtained by analyzing the width and the symmetry of the "far-field" laser beam by geometrical beam splitting in the two slightly tilted, concave "half-ring" reflectors 23a,b surrounding the circular concave reflector 24. In principle, comparison of the center beam and the side beams yields the focus error signal, whereas the tracking error signal is obtained from the difference of the side beams; other combinations can be used as well.

Figure 6:
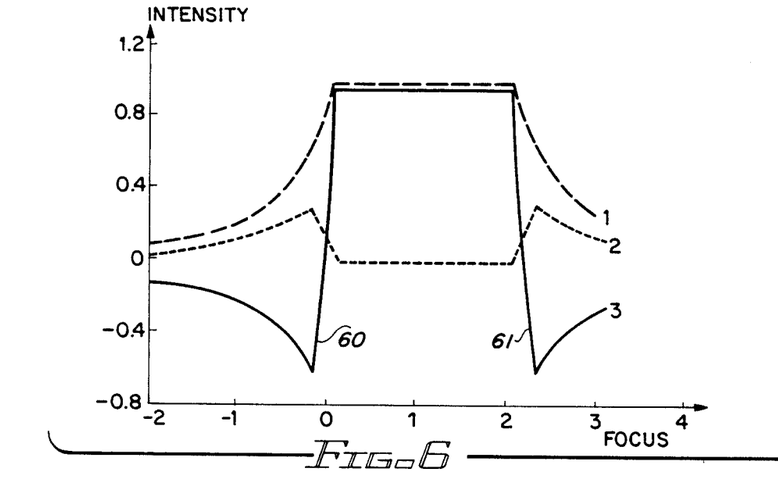
FIG. 6 shows a schematic diagram of the focus servo-control signal generated by the arrangements of FIG. 5.

FIG. 6 shows the focus servo signal obtained in the far field of the light beams. Curve 1 represents the output of detectors that measure the light intensity in the central part of the beam as a function of the focus state; curve 2 is the output signal of a ring-shaped detector measuring peripheral intensities. Curve 3, to be used as servo signal, is obtained by electronically subtracting curve 2 (after multiplication by a constant factor) from curve 1. The steep edges 60,61 then provide a sensitive servo signal which has a great capture range and is direction sensitive. These advantages are not available in conventional servo systems based on the evaluation of beam astigmatism with a four-quadrant photodetector.

Analysis of the beam shape to extract servo control signals is not restricted, however, to an annular geometry, but can also be performed using a stripe geometry where the power distribution across the beam is measured with slit rather than annular apertures. It can be shown that a certain amount of defocus in the beam will produce the same variations of the radially or the linearly-integrated power distribution across the beam.

This characteristic can be put to advantage in the design of the reflecting elements in beam analyzer 3. The assembly of tilted mirrors 23,24 can be replaced by a multiple stripe reflector, each stripe having an image-forming surface and all stripes facing the same direction. The stripe boundaries are oriented parallel to PBS layer 26.

Figure 8:
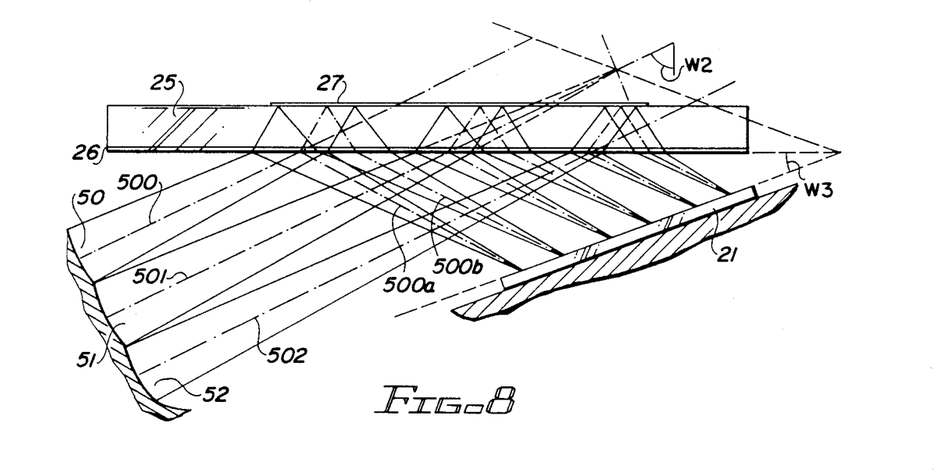
FIG. 8 shows in schematic representation a second embodiment of the integrated beam analyzer in accordance with the invention using striped reflectors.

FIG. 8 shows in schematical representation the paths of the three convergent beams 500, 501 and 502 emerging from a stripe reflector with three parabolic surfaces 50, 51 and 52. The partial beams are again split by PBS layer 26 in two beams each, e.g. 500a, 500b, which are reflected at PBS 26 and reflective coating 27, respectively, to impinge on photodetector array 21; the latter is oriented obliquely to compensate for the different optical paths in the partial beams, e.g. 500a, 500b. In an embodiment, angles W2 and W3 were chosen as 65 degrees and 20 degrees, respectively.

The foci of all partial beams indicated in the optical setup of FIG. 8 are colinear in the plane of photodetector array 21 and separated according to the separation of the mirror stripes and the tilt of the detector plane. Preferably, the stripe reflectors should be arranged such that the tracks on the magnetooptic disk, as seen from the beam analyzer, are oriented at 45 degrees with respect to the normal of PBS layer system 26. Other orientations are, however, also possible as sensitivity follows a cosine law without severe degradation of performance in a large range of angles.

Figure 11A:
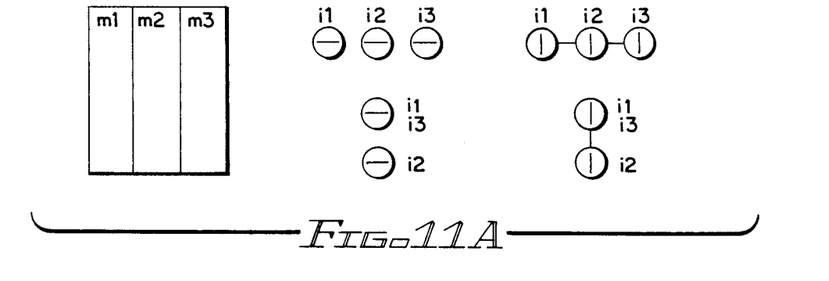
FIGS. 11A, B and C show different geometries of the stripes of the second embodiment of FIG. 8.
Figure 11B:
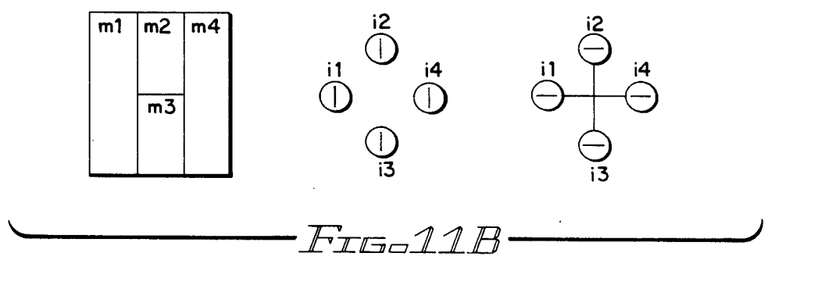
Figure 11C:
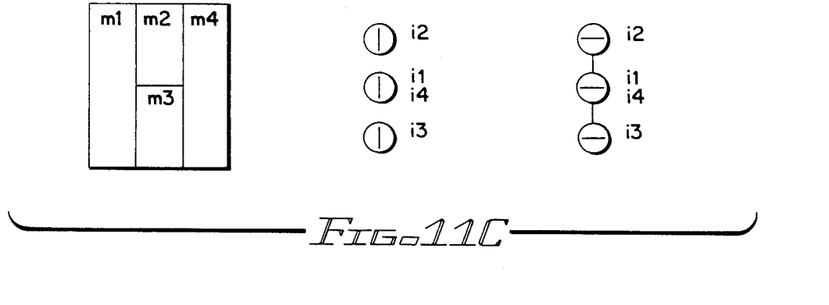

FIGS. 11A-C show different stripe geometries and associated detector arrangements; the stripes or mirrors are designated by m1,m2 ... and their corresponding foci by i1,i2, ... Photodetectors are shown by circles with an indication of the polarization of the light which they receive.

The simple three-stripe arrangement of FIG. 11A allows focus detection in the far field and uses, in a first alternative 6, photodetectors: Three individual detectors receiving foci i1-i3 and three interconnected detectors (or one single detector) to measure the total intensity of the other polarization direction. This arrangement is suitable for an optical disk with sector servo means, where no track control is required. In the second embodiment, only two detectors are used for each polarization direction when stripe mirrors m1 and m3 are adjusted to have their foci i1,i3 on one detector.

FIG. 11B shows a modified stripe arrangement where the central stripe is split and the two halves slightly titled; this configuration allows left/right distinction and can thus be used for track control. Four detectors are required for one polarization detector and one detector for the sum of the beams with the other polarization.

FIG. 11C shows a modification of FIG. 11B with one diode less for each polarization direction, thus saving costs for diodes and associated electric circuitry. As an alternative to the stripe geometries of FIGS. 11B,C, split detectors can be used for left/right discrimination.

Using a stripe· reflector instead of the annular arrangement of FIG. 2 yields a number of significant advantages:

the manufacture of the reflector mold in substrate 20 is simplified;

greater positional tolerance is obtained for the incident beam in parallel to the stripes;

angular tolerance requirements for PBS layer 26 are reduced;

the second mirror (22 in FIG. 2A) is no longer necessary.

The advantage of increased angular tolerance for the polarizing beam-splitter layer 26 is of considerable importance for the design of the integrated beam analyzer in accordance with the invention. The compact dimensions of this analyzer require the polarization-sensitive beam splitting (by PBS layer 26) to be performed in a convergent beam; therefore, an "angle tolerant" design for PBS layer 26 is required. This calls for a special design of this layer as conventional polarizing beam-splitting layers are highly angle sensitive. In addition, there is a trade-off between the angular tolerance of a multilayer polarizing beam splitter and the tolerable range of light wavelengths: Strongly divergent beams require a better control of the wavelength range and thus more expensive lasers.

The use of a multiple stripe mirror allows to reduce the typical range of angles of incidence from ±9 degrees in the embodiment of FIGS. 2A-E to about ±3 degrees, of the embodiment of FIG. 8, thus offering a wider wavelength range and more freedom for the design and the tolerances of PBS layer 26.

A structure of stacked dielectric layers forming the PBS layer 26 is now described in detail that meets the requirements for a large range of angles of incidences and can be used for the beam analyzer of the subject invention. It is based on the known principle of polarization-dependent reflectance at oblique incidence in the vicinity of the Brewster angle: The p component, i.e. the component with the E vector parallel the plane of incidence, will be transmitted through the beam splitting surface, whereas the s component orthogonal thereto will be reflected only partially. A complete separation of p and s components requires a large number of interfaces (up to 50) making such a system very sensitive to small deviations in the angle of incidence and in the wavelength of the incident light. The allowed deviations are, therefore, in the order of some degrees only.

The novel sequence of dielectric layers with different indices of refraction achieves that the s component reflected at all the dielectric interfaces will add together while the p components have an effective sum close to zero. Three effective reflected amplitudes, from the air/top-layer interface and from two stacks of dielectric layers are used together with phase-matching layers such that the desired p and s light behavior will be produced. The general configuration of this novel layer sequence referring to Table I and FIG. 12A is as follows:

A "lower stack" of alternating layers L2-8 on a glass substrate L1;

an intermediate layer L9 with increased thickness to compensate the phase shift (of about 50 degrees) between the effective beams reflected at the upper and lower stacks, respectively;

an "upper stack" of further layers L10-16 deposited on the intermediate layer L9;

a "thick layer" L17 deposited on the upper stack L10-16 to compensate the phase shift at the air/top-layer interface;

optionally, one or two "top-layers" L18-19 deposited on the "thick layer" L17 to match the amplitude of the air/top-layer reflection.

Dimensions of such a system with nineteen layers are reproduced in Table I; $SiO_2$ and $ZrO_2$, respectively, are used for the alternating layers in view of their widely-diverting index of reflection to keep the number of layers in the lower and upper stack as low as possible.

Figure 9A:
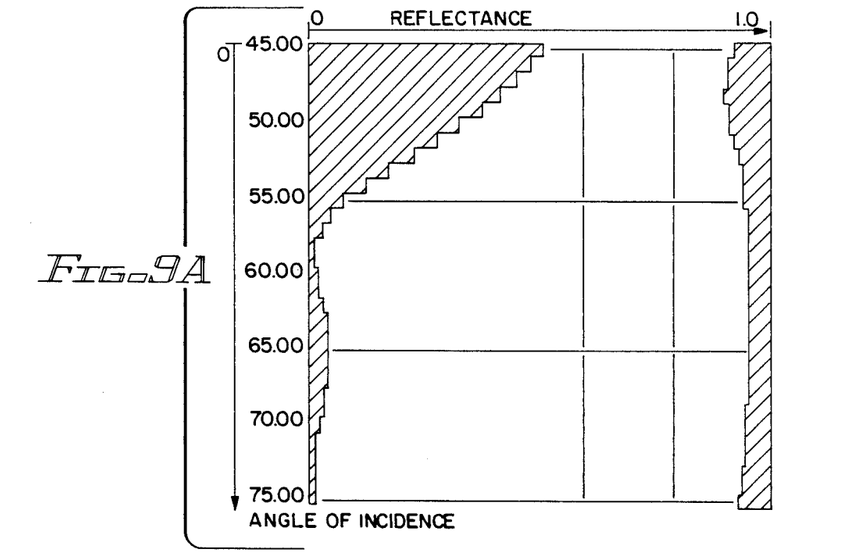
FIGS. 9A,B show diagrams for the reflected intensities in two orthogonal polarization directions as a function of the angle of incidence when a beam of light is reflected at a polarizing beam-splitter layer system in accordance with the invention.
Figure 12A:
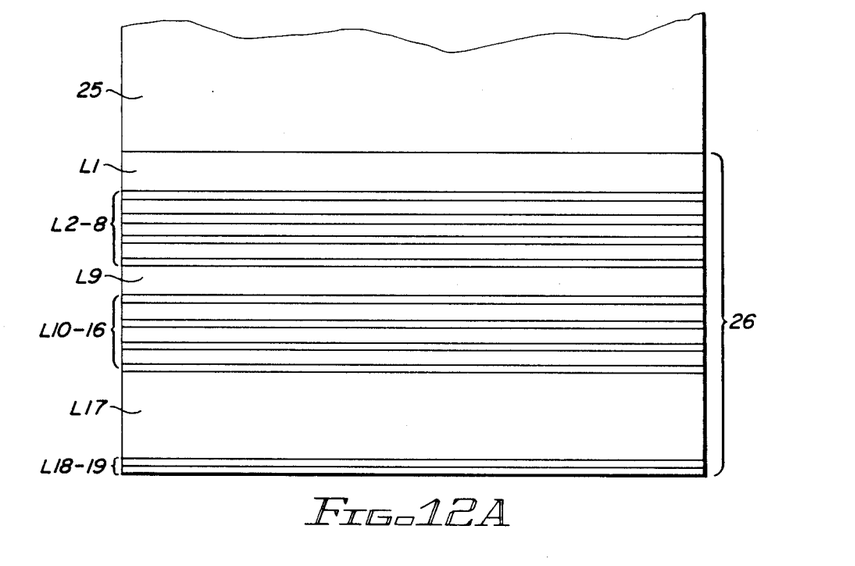
FIGS. 12A and B show the layered structure of the polarizing beam-splitter layer system in accordance with the present invention.

The polarization beam-splitting behavior of this sequence of nineteen layers of FIG. 12A is schematically indicated in FIG. 9A; it is evident that for angles of light incidence between 55 and 75 degrees, the average p reflectance is 2.2%, while the average s reflectance is 96.0%, such that almost complete separation of the two polarization directions is achieved.

Figure 9B:
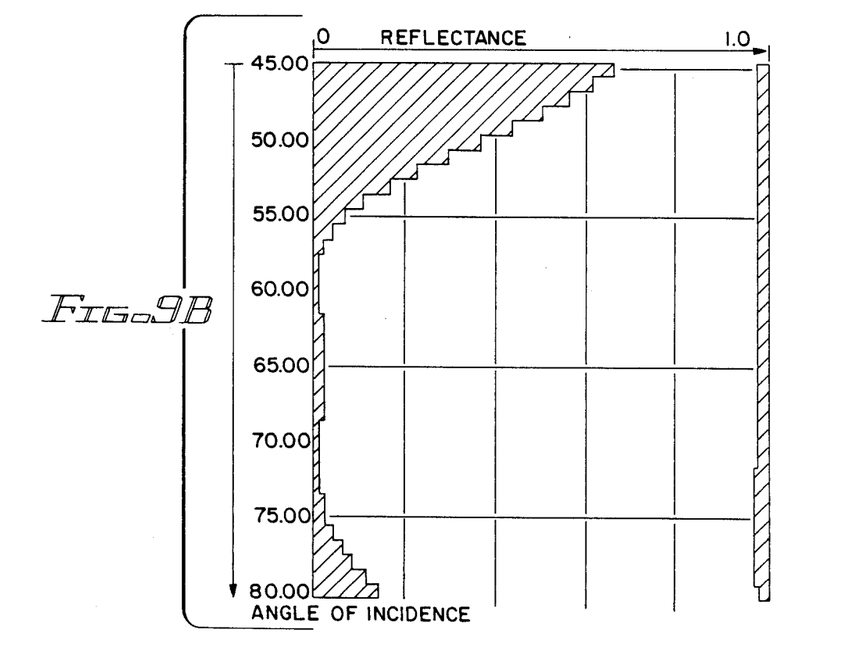
Figure 12B:
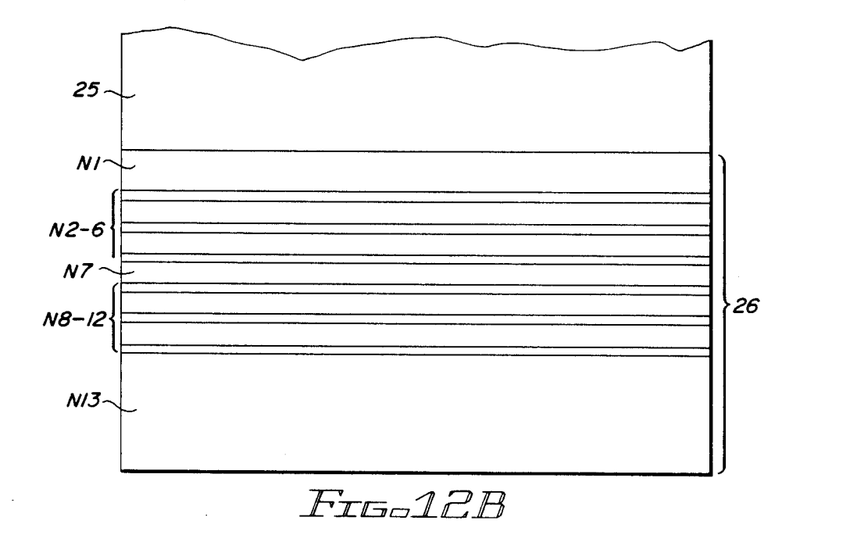

An alternate embodiment with 13 layers of $SiO_2$ and $TiO_2$ is described in Table II and FIGS. 9B and 12B; no special top layers are used there. The average transmittance in the range between 55 and 75 degrees is 0.986 for the p component and 0.026 for the s component. A plurality of alternate lower stack layers N2-6 of $TiO_2$ and $SiO_2$ are deposited on the glass substrate N1. An intermediate layer N7 of $SiO_2$ separates the lower stack layers N2-6 from a plurality of upper stack layers N8-12 of $TiO_2$ and $SiO_2$. The upper stack layers N8-12 are covered by a thick layer N13 of $SiO_2$.

TABLE I

| Layer | Material | Thickness/nm | Index of refraction | |
|---|---|---|---|---|
| L1 | GLASS, | ***** | n = 1.513 | substrate |
| L2 | $ZrO_2$, | 80 | n = 2.236 | |
| L3 | $SiO_2$, | 140 | n = 1.453 | |
| L4 | $ZrO_2$, | 80 | n = 2.236 | |
| L5 | $SiO_2$, | 140 | n = 1.453 | lower stack |
| L6 | $ZrO_2$, | 80 | n = 2.236 | |

TABLE I-continued

| Layer | Material | Thickness/nm | Index of refraction | |
|---|---|---|---|---|
| L7 | $SiO_2$, | 140 | n = 1.453 | |
| L8 | $ZrO_2$, | 80 | n = 2.236 | |
| L9 | $SiO_2$, | 195 | n = 1.453 | intermediate layer |
| L10 | $ZrO_2$, | 80 | n = 2.236 | |
| L11 | $SiO_2$, | 140 | n = 1.453 | |
| L12 | $ZrO_2$, | 80 | n = 2.236 | |
| L13 | $SiO_2$, | 140 | n = 1.453 | upper stack |
| L14 | $ZrO_2$, | 80 | n = 2.236 | |
| L15 | $SiO_2$, | 140 | n = 1.453 | |
| L16 | $ZrO_2$, | 80 | n = 2.236 | |
| L17 | $SiO_2$, | 750 | n = 1.453 | thick layer |
| L18 | $ZrO_2$, | 55 | n = 2.236 | top layers |
| L17 | $SiO_2$, | 20 | n = 1.453 | |
| 20 | AIR, | ***** | n = 1.000 | |

TABLE II

| Layer | Material | Thickness/nm | Index of refraction | |
|---|---|---|---|---|
| N1 | GLASS, | ***** | 1.513 | substrate |
| N2 | $TiO_2$, | 56 | 2.646 | |
| N3 | $SiO_2$, | 140 | 1.453 | |
| N4 | $TiO_2$, | 56 | 2.646 | lower stack |
| N5 | $SiO_2$, | 140 | 1.453 | |
| N6 | $TiO_2$ | 56 | 2.646 | |
| N7 | $SiO_2$ | 200 | 1.453 | intermediate layer |
| N8 | $TiO_2$ | 56 | 2.646 | |
| N9 | $SiO_2$ | 140 | 1.453 | |
| N10 | $TiO_2$ | 56 | 2.646 | upper stack |
| N11 | $SiO_2$ | 140 | 1.453 | |
| N12 | $TiO_2$ | 56 | 2.646 | |
| N13 | $SiO_2$ | 820 | 1.453 | thick layer |
| N14 | AIR, | ***** | 1.000 | |

Although magnetooptic storage devices are the preferred field of use for the beam analyzer and the polarizing beam splitter of the invention, both components can be used in various other applications, where polarized beams have to be generated and analyzed.

While the invention has been particularly shown and described with reference to preferred embodiment thereof, it will be understood by those skilled in the art that various changes in form and details may be made therein without departing from the spirit and scope of the invention:

What is claimed is:

1. An analyzer for determining the polarization state of a light beam comprising:
   a laser to generate a collimated light beam;
   focusing lens to direct the collimated light beam to a magneto-optical disk;
   an optical glass plate;
   a polarizing beam splitter formed on a first surface of said optical glass plate;
   said beam splitter having a plurality of lower stack alternating dielectric layers, an intermediate dielectric layer, a plurality of upper stack alternating dielectric layers and a thick dielectric layer deposited on the upper stack dielectric layers;
   one alternating dielectric layer having a different index of refraction from its adjacent alternating dielectric layer, such that the component reflected at all dielectric layers add together and have a P reflective component having an effective sum close to zero; and
   means to direct the light beam reflected from the magneto-optical disk to said optical polarizing beam splitter.

2. An analyzer as defined in claim 1, wherein said optical glass plate has an index of refraction of 1.513 and wherein said polarizing beam splitter includes a plurality of stacks of dielectric layers comprising:

said lower stack and said upper stack, each having seven dielectric layers with the odd alternating layers each made of a $ZrO_2$ layer, with a thickness of 80 nm and a refraction index of 2.236 and the even alternating layers made of a $SiO_2$ layer with a thickness of 140 nm and a refraction index of 1.453, which are alternately stacked on each other, respectively;

said intermediate layer separating said lower stack layers and said upper stack layers including a $SiO_2$ layer with a thickness of 195 nm and a refraction index of 1.453;

said thick layer covering said upper stack layers including a $SiO_2$ layer having a thickness of 750 nm and a refraction index of 1.453; and further including top layers having a $ZrO_2$ layer deposited on said thick layer and having a thickness of 55 nm and a refraction index of 2.236 and a $SiO_2$ layer deposited on the $ZrO_2$ layer and having a thickness of 20 nm and a refraction index of 1.453.

3. An analyzer as defined in claim 1 wherein said optical glass plate has an index of refraction of 1.513, and wherein the plurality of layers of said beam splitter comprise:

said lower stack and said upper stack layers each includes five alternating dielectric layers with the odd dielectric layers including a $TiO_2$ layer with a thickness of 56 nm and a refraction index of 2.646 and the even layers having a $SiO_2$ layer with a thickness of 140 nm and a refraction index of 1.453, which are alternately stacked on each other, respectively;

said intermediate layer separating said lower stack and said upper stack, includes an $SiO_2$ layer with a thickness of 200 nm and a refraction index of 1.453;

said thick layer covering said upper stack includes a $SiO_2$ layer having a thickness of 820 nm and a refraction index of 1.453.

4. An analyzer as defined in claim 1 further including a tilted mirror and a first and a second photodetector, and wherein:

said means to direct the light beam reflected from the magnetooptical disk, directs the reflected light beam in a first oblique angle to a second surface of said optical glass plate and is reflected by said tilted mirror to be redirected to said polarizing beam splitter under a second oblique angle of incidence, said plane of polarization of the beam reflected by said tilted mirror, being rotated by said polarizing beam splitter;

said first photodetector detecting a first partial beam emerging from said polarizing beam splitter directly; and said second detector detecting a second partial beam after reflection at the top surface of said optical glass plate.

5. The analyzer of claim 4 wherein said tilted mirror is circular and surrounded by an annular imaging mirror.

* * * * *